(12) United States Patent
Turri

(10) Patent No.: US 11,318,142 B2
(45) Date of Patent: May 3, 2022

(54) PHARMACEUTICAL FORMULATION FOR USE IN THE TREATMENT OF DEPRESSIVE AND ANXIETY DISORDERS

(71) Applicant: Milo Turri, Barga (IT)

(72) Inventor: Milo Turri, Barga (IT)

( * ) Notice: Subject to any disclaimer, the term of this patent is extended or adjusted under 35 U.S.C. 154(b) by 85 days.

(21) Appl. No.: 15/733,538

(22) PCT Filed: Mar. 1, 2019

(86) PCT No.: PCT/IB2019/051650
§ 371 (c)(1),
(2) Date: Aug. 21, 2020

(87) PCT Pub. No.: WO2019/167004
PCT Pub. Date: Sep. 6, 2019

(65) Prior Publication Data
US 2021/0085687 A1    Mar. 25, 2021

(30) Foreign Application Priority Data

Mar. 2, 2018  (IT) .................... 102018000003223

(51) Int. Cl.
| | |
|---|---|
| *A61K 31/55* | (2006.01) |
| *A61P 25/22* | (2006.01) |
| *A61P 25/24* | (2006.01) |
| *A61K 9/00* | (2006.01) |
| *A61K 9/20* | (2006.01) |
| *A61K 9/48* | (2006.01) |
| *A61K 31/137* | (2006.01) |

(52) U.S. Cl.
CPC ............ *A61K 31/55* (2013.01); *A61K 9/0053* (2013.01); *A61K 9/20* (2013.01); *A61K 9/48* (2013.01); *A61K 31/137* (2013.01); *A61P 25/22* (2018.01); *A61P 25/24* (2018.01)

(58) Field of Classification Search
CPC ........ A61K 31/55; A61K 9/0053; A61K 9/20; A61K 9/48; A61K 31/137; A61P 25/22; A61P 25/24
See application file for complete search history.

(56) References Cited

FOREIGN PATENT DOCUMENTS

| | | |
|---|---|---|
| WO | 2004091580 | 10/2004 |
| WO | 2007129329 | 11/2007 |
| WO | 2017213977 | 12/2017 |

OTHER PUBLICATIONS

S. Mohapatra et al., "Opipramol: A Novel Drug," DElhi Psychiatry Journal, vol. 16, No. 2 (Oct. 2013), pp. 409-441 The whole document.

*Primary Examiner* — Sahar Javanmard
(74) *Attorney, Agent, or Firm* — Themis Law

(57) ABSTRACT

The present invention is aimed at a novel composition for use as a medicament; it is also aimed at said composition for use in the treatment of depressive and anxiety syndromes. In particular, said composition is for use in the treatment of: major depression, generalized anxiety disorder, social phobia, panic disorder, mixed depression and anxiety disorder, somatoform disorder, treatment-resistant depression, obsessive-compulsive disorder. The invention also relates to a process for the preparation of said pharmaceutical composition.

10 Claims, No Drawings

PHARMACEUTICAL FORMULATION FOR USE IN THE TREATMENT OF DEPRESSIVE AND ANXIETY DISORDERS

TECHNICAL FIELD OF THE INVENTION

The present invention is aimed at a novel composition (pharmaceutical) for use as a medicament; in particular, the present invention is aimed at the above pharmaceutical composition for use in the treatment of depressive and anxiety syndromes. Specifically, said pharmaceutical composition is suitable for use in the treatment of: major depression, generalized anxiety disorder, social phobia, disorder, panic disorder, mixed depression and anxiety disorder, somatoform disorder, treatment-resistant depression, obsessive-compulsive disorder. The invention also relates to a process for the preparation of said composition.

BACKGROUND OF THE INVENTION

The data relating to the incidence of depressive syndromes, in particular of major depression with or without anxiety component, in the general population have reached dramatically high levels with costs associated with treatments and loss of productivity amounting to several billion dollars. Patients who, despite adequate therapy, do not fully recover or worse, fail to respond at all to the treatments, are estimated at more than a third of subjects in treatment. From WHO data, depression affects 322 million people worldwide. Depression as a whole is the foremost item of expenditure of the healthcare systems of European countries. The majority of people suffering from depression (major depression according to the DSM-V) are of full working age, and the loss of productivity associated with this condition has been estimated at one trillion US dollars per year. Despite the treatments available to date, well over a third of patients in therapy for depressive, anxiety, or mixed disorders or do not attain complete remission, and a sizeable proportion of these obtain no response in terms of improvement.

From these concerns emerges the need to have new and more effective pharmacological strategies available.

Brief Description of the Prior Art

Research in this field has been directed toward the identification of new target receptors besides the "conventional" monoaminergic receptors (receptors 5HT2A, 5HT2C, 5HT1A, 5HT7, α2 and β2, D2, D3, H1, and so on) the activities of which are acted upon by tricyclic antidepressants (TCAs), monoaminoxidase inhibitors (MAOIs), and selective serotonin reuptake inhibitors (SSRIs), or serotonin and noradrenaline reuptake inhibitors (SNRI), of dopamine and noradrenaline (DNRIs) by increasing the bioavailability of the neurotransmitter at the synaptic level.

Among the target receptors investigated, one that has aroused great interest is the receptor called sigma-1 (σ-1), just recently discovered and initially erroneously included in the family of opioid receptors. Today it is known that the σ-1 receptor endogenously binds neurohormones having a steroidal structure such, for example, dehydroepiandrosterone sulphate (DHEAS) and progesterone. Also many exogenous compounds, including SSRIs, bind, with different affinity levels, to the σ-1 receptor as agonists.

The role of these receptors in the treatment of depression has been elucidated by studies demonstrating how they are capable of modulating serotoninergic, dopaminergic, and, especially, glutamatergic transmission in strategic areas of the central nervous system (CNS) such, for example, the limbic system, the anterior cingulate cortex, the amygdala and the hippocampus (Jordanna E. Bermack and Guy Debonnel, 2004 J Pharmacol Sci 97, 317-336 (2005) *The role of Sigma Receptors in depression*. Jordanna E. Bermackl and Guy Debonnell,* 1 Department of Psychiatry, McGill University, 1033, Pine Avenue West, Suite 207, Montreal, Quebec, Canada H3A 1A1. Received Nov. 22, 2004). They are also capable of influencing the flow of calcium ions across the membrane in nerve cells, by modifying their action potential and thus their excitability (normalization of calcium flows within neurons is one of the mechanisms underlying the activity of various mood stabilizing drugs).

The glutamatergic system has still not been fully exploited as a target for the action of antidepressant and/or anxiolytic drugs. The only drugs developed by research for this system, and moreover with limited effectiveness, given the pathologies to which they are addressed, are Memantine for Alzheimer's disease and Riluzole for amyotrophic lateral sclerosis (ALS). The fact that via an agonist action on the σ-1 receptor this system can also be "manipulated" to obtain an antidepressant/anxiolytic effect is an absolute novelty. Moreover, SSRIs (and other molecules) also have agonist activity on this receptor, in particular fluvoxamine followed, in terms of affinity, by sertraline (in order of decreasing affinity, these are followed by fluoxetine, citalopram, and paroxetine). However, clinical experience teaches that notwithstanding the use of high dosages of these known drugs in therapy, these alone do not resolve cases that are refractory to treatment. For this a stronger σ-1 receptor agonist could yield better results. Such a molecule exists and is used in particular in Germany and other European countries for the treatment of generalized anxiety disorder (GAD), generally as the monotherapy. Said molecule corresponds to 4-[3-(5H-dibenz[b,f]azepine-5-yl)propyl]-1-piperazinethanol, a tricyclic antidepressant compound known as Opipramol.

Agonist action on the σ-1 receptor through binding to opipramol causes the migration of the receptor complex from the endoplasmic reticulum of the nerve cell to the cytoplasmic membrane thereof, where it performs a sensitization of permeability to calcium ions ($Ca^{2+}$). Increased influx of calcium ions into the glutamatergic neuron determines the release therefrom of neurotransmitters such as serotonin and noradrenaline, dopamine, glutamate and acetylcholine on the synaptic gradient, with increase of neurotransmission. No other drug currently available guarantees the synaptic release of all these neurotransmitters, in particular of glutamate and acetylcholine, which positively influence both mood and cognitive functions.

Moreover, σ-1 receptor agonism is capable of initiating a series of intracellular events, including an increase in the production of the transcription factor CREB which involves an increase in the production of BDNF (Brain-derived neurotrophic factor). This, as is well known, is capable of stimulating neurogenesis in particular areas of the CNS, including the hippocampus. Hippocampal atrophy is correlated to patients with major depression and is in all probability due both to the regression of dendritic processes and to a real loss of hippocampal neurons. Recent studies have shown that the σ-1 receptors are also co-involved in the budding of an axon and in its branching (or sprouting). Yet the same study has highlighted how SSRIs are able to increase the density of these receptors in these affected areas (Takebayashi M., Hayashi T., on T. P., *nerve growth factor-induced neurite sprouting in PC12 cells involves sigma-1* receptors: implications for antidepressants. J Pharmacol Exp Ther 2002; 303, 1227-1237).

For its part, the compound (RS)-1-[2-dimethylamino-1-(4-methoxyphenyl)-ethyl]cyclohexanol, an antidepressant of the class of SNDRIs known as venlafaxine, proved to be one of the most effective antidepressants in major depressions, has a good affinity for the σ-1 receptor, inhibits the reuptake of serotonin and noradrenaline and, at higher dosages, of dopamine also.

TECHNICAL PROBLEM

Unfortunately, even the use of these last two compounds, taken individually, at dosages known and commonly used in therapy has not been completely satisfactory for the resolution of the problems described previously, both in respect of the treatment of all the depressive and anxiety syndromes described and, in particular, in respect of the cases that are refractory to known treatments. There remains, therefore, the need in medical circles to have available new pharmaceutical compositions having adequate antidepressant and/or anxiolytic activity, that are able to provide a satisfactory response to the problems previously described.

SUMMARY OF THE INVENTION

The Applicant has now found that, by combining suitable quantities of Opipramol and Venlafaxine, it is possible to give an adequate response to the technical problem generated by the need described above.

One object of the present invention is therefore a suitable combination of the two active principles referred to above for use as a medicament, as stated in the attached independent claim.

Another object of the present invention is then formed by a pharmaceutical composition comprising the combination of said two active principles referred to above, as stated in the attached independent claim.

Yet another object of the present invention is a pharmaceutical composition comprising the aforementioned combination for use in the treatment of depressive and anxiety syndromes, as stated in the attached independent claim.

A still further object of the present invention is a process for preparing said composition referred to above, as stated in the attached independent claim.

Other objects of the present invention are described in the appended dependent claims.

DETAILED DESCRIPTION OF THE INVENTION

The present invention is aimed at a combination of Opipramol and Venlafaxine, for use as a medicament, wherein:

Opipramol is present in an effective amount comprised from 60 to 200 mg (i.e. from 0.165 to 0.550 mmol); preferably, from 80 to 180 mg; more preferably, from 100 to 160 mg; even more preferably, from 100 to 140 mg; even more preferably, from 100 to 120 mg; as, for example, of 100 mg or 120 mg, if said compound is considered as free base (molecular weight Mw=363.50);

Venlafaxine is present in an effective amount ranging from 75 to 225 mg (from 0.270 to 0.811 mmol); preferably, from 80 to 200 mg; more preferably, from 80 to 180 mg; even more preferably, from 80 to 160 mg; even more preferably, from 80 to 140 mg; as, for example, 80 mg or 140 mg, if said compound is considered as free base (molecular weight Mw=277.40).

In a preferred embodiment, the pharmacologically used form for Opipramol is its dihydrochloride salt (molecular weight Mw=436.42). Consequently, in this case, opipramol, in the form of the dihydrochloride, will be present in an amount ranging from 72 to 240.03 mg; preferably, from 96.05 to 240.12 mg; more preferably, from 96.05 to 216.11 mg; even more preferably, from 96.05 to 168.08 mg; as, for example, of 96.05 mg or 216.11 mg.

In a preferred embodiment, the pharmacologically used form of venlafaxine is its hydrochloride salt (molecular weight Mw=313.87). Consequently, in this case, venlafaxine, in the form of the hydrochloride, will be present in an amount ranging from 84.86 to 254.58 mg; preferably, from 90.52 to 226.29 mg; more preferably, from 90.52 to 203.66 mg; even more preferably, from 90.52 to 181.03 mg; even more preferably from 90.52 to 158.40 mg; as, for example, of 90.52 mg or 158.40 mg.

The present invention is further aimed at a pharmaceutical composition comprising the aforesaid combination of opipramol and venlafaxine as the active principle, for use as a medicament, wherein:

Opipramol is present in an effective amount ranging from 60 to 200 mg (i.e. from 0.165 to 0.550 mmol); preferably, from 80 to 180 mg; more preferably, from 100 to 160 mg; even more preferably, from 100 to 140 mg; even more preferably, from 100 to 120 mg; as, for example, of 100 mg or 120 mg, if said compound is considered as free base (molecular weight Mw=363.50);

Venlafaxine is present in an effective amount ranging from 75 to 225 mg (from 0.270 to 0.811 mmol); preferably, from 80 to 200 mg; more preferably, from 80 to 180 mg; even more preferably, from 80 to 160 mg; even more preferably, from 80 to 140 mg; as, for example, 80 mg or 140 mg, if said compound is considered as free base (molecular weight Mw=277.40).

In a preferred embodiment, the pharmacologically used form of opipramol is its dihydrochloride salt (molecular weight Mw=436.42). Consequently, in this case, opipramol, in the form of the dihydrochloride, will be present in an amount ranging from 72 to 240.03 mg; preferably, from 96.05 to 240.12 mg; more preferably, from 96.05 to 216.11 mg; even more preferably, from 96.05 to 168.08 mg; as, for example, of 96.05 mg or 216.11 mg.

In a preferred embodiment, the pharmacologically used form of venlafaxine is its hydrochloride salt (molecular weight Mw=313.87). Consequently, in this case, venlafaxine, in the form of the hydrochloride, will be present in an amount ranging from 84.86 to 254.58 mg; preferably, from 90.52 to 226.29 mg; more preferably, from 90.52 to 203.66 mg; even more preferably, from 90.52 to 181.03 mg; even more preferably from 90.52 to 158.40 mg; as, for example, of 90.52 mg or 158.40 mg.

The pharmaceutical composition of the present invention may further comprise excipients, co-formulants, additives, preservatives, adjuvants, charges, fillers, and so forth, commonly known and used in the art of pharmaceutical formulation.

The pharmaceutical composition of the present invention is preferably for oral administration; preferably, in the form of tablets, lozenges, pastilles, pills, soft or hard capsules, and so forth; optionally, in a gastro resistant coated or protected form, or in a controlled release form in such a way as to obtain a modulated release over a total of 24 hours (which would make it possible to deliver a single administration per day, as highly preferred).

In a preferred embodiment, said pharmaceutical composition is in the form of a tablet or a capsule.

In another preferred embodiment, said pharmaceutical composition is in a controlled release form.

The pharmaceutical composition of the present invention is for the use in the treatment of depressive and anxiety syndromes. In one embodiment of the invention, said pharmaceutical composition of the invention is for use in the treatment of: major depression, generalized anxiety disorder, social phobia, disorder, panic disorder, mixed depression and anxiety disorder, somatoform disorder, treatment-resistant depression, obsessive-compulsive disorder.

In one embodiment of the invention, the combination of the two active principles in the pharmaceutical composition consists of:

Opipramol 120 mg (0.330 mmol), if calculated as a free base; or 152.98 mg as a dihydrochloride salt;

Venlafaxine 140 mg (0.505 mmol), if calculated as a free base; or 158.40 mg as a hydrochloride salt.

In this case, the pharmaceutical composition is preferably for use in the treatment of: major depression, Mixed depression and anxiety disorder, obsessive-compulsive disorder.

In another embodiment of the invention, the combination of the two active principles in the pharmaceutical composition consists of:

Opipramol 100 mg (0.275 mmol), if calculated as a free base; or 120.01 mg as a dihydrochloride salt;

Venlafaxine 80 mg (0.288 mmol), if calculated as a free base; or 90.52 mg as a hydrochloride salt.

In this case, the pharmaceutical composition is preferably for use in the treatment of: generalized anxiety disorder, panic disorder, social phobia, somatoform disorder.

The preparation of the pharmaceutical composition of the present invention is carried out using the equipment and the working methods that are commonly used in pharmaceutics for the production of oral pharmaceutical forms such as those mentioned above; these will therefore not be explained here since they are well known to those skilled in the art who, on the basis of their personal knowledge, will have no difficulty in applying them to prepare the above compositions.

The mono administration of SSRIs has been one of the factors that has caused the therapy in patients with a diagnosis of depression to be perceived as more acceptable and easy to follow, with large increases in compliance as compared with the administration divided into a plurality of daily doses which was, for example, indicated for the tricyclic antidepressants.

On the other hand the more complex therapies, which involve a greater number of drugs with more daily doses, register the highest rates of drop-out and therefore of therapeutic failure. Hence the need for and the advantages of a sustained release, single-dose formulation (for example, a single tablet) of the two active principles; furthermore, the half-life of opipramol is only of 6-11 hours and the one of venlafaxine is approximately of 7 hours, a fact that renders the 24-h sustained release a necessity.

For a sustained release preparation, the usual method of dispersing the active ingredient in a mixture of methacrylates is used (see *Acrylic acid-methyl methacrylate copolymer for prolonged oral drug release*. Vijay S. et al., J Mater Sci MATER MED 2010).

By comparison with the agonist action exhibited by the SSRIs and SNRIs, a stronger agonist action on the σ-1 receptor seems to be the key to a more intense and rapid antidepressant and anxiolythic action, which for the first time in the clinical treatment of depression, also involves the glutamatergic system.

Moreover, the increase in serotonin and noradrenaline at the synaptic level guaranteed by venlafaxine maximizes the neurotransmission reactivation necessary for the antidepressant action. The simultaneous involvement of these monoaminergic and receptor systems also entails an increase in the intracerebral production of BDNF and therefore an increase in neurogenesis, with a more rapid and complete recovery of the higher functions of the depressed patient (cognitive ability, memory, resistance to psychic application). This combined approach in clinical practice represents an absolute novelty.

Experimental Data and Clinical Considerations

Evaluation of the Clinical Synergic Efficacy of the Opipramol/Venlafaxine Combination of the Present Invention Under Various Psychopathological Conditions in which Said Combination is Indicated.

Below we describe a series of outpatient drug treatments; and the results obtained are reported and discussed.

44 patients were admitted to receive the drug treatment with opipramol/venlafaxine (O/V). Of these, 12 were affected by treatment-resistant depression; 12 were patients with disabling panic disorder; 10 had severe obsessive-compulsive disorder; 10 were included in the so called "anxiety" group, comprising both cases of generalized anxiety disorder and somatized anxiety.

The severity of each individual diagnosis was established through the use of known evaluation scales accredited, in particular:

for patients with treatment-resistant depression, the so-called Montgomery-Åsberg Depression Rating Scale (MADRS) was used; all patients of this group had an admission to study score>34 (severe depression);

for patients with disabling panic disorder, the initial score was attributed using the so-called Panic Disorder Severity Scale (PDSS), and was between 18 and 24 (markedly severe disturbance);

for patients with obsessive-compulsive disorder, the score was attributed on the basis of the rating scale known as the Yale-Brown Obsessive-compulsive Scale (Y-BOCS); at the time of entry into the study, nine of these had a score >24 but <30 (serious disorder), while one patient had a score of 32 (corresponding to extremely severe disturbance);

for the patients in the "anxiety" group, the score was attributed on the basis of the so-called Hamilton Anxiety Rating Scale (HAM-A); these had an initial score of between 22 and 26.

The sample consisted of 22 men and 22 women of Caucasian race, aged between 22 and 76 years. All the patients had already experienced therapies with two or more known antidepressants, taken consecutively or in combination, or therapies involving combinations of antidepressants and benzodiazepine anxiolytics, following which none had achieved remission or an improvement in the symptoms deemed significant. In this respect, for each category of patient, the reduction in symptoms was considered as "markedly improved" if superior than 75%, as "improved" if between 40% and 74%, and if comprised within the range from 10% to 39% it was considered as a minimal (insufficient) improvement. No patient enlisted had achieved a reduction in symptoms exceeding 40% with the previous therapies.

TABLES of the rating scales used

| SCORE | CLINICAL SEVERITY |
|---|---|
| 1.a) Montgomery-Åsberg Depression Rating Scale (MADRS) | |
| Less than 6 | Depressive symptoms absent |
| From 7 to 19 | Mild depression |
| From 20 to 34 | Moderately severe depression |
| >34 | Severe depression |
| 1.b) Panic Disorder Severity Scale (PDSS) | |
| Less than 4 | Symptoms absent |
| From 4 to 5 | Borderline symptoms |
| From 6 to 9 | Mild Symptoms |
| From 10 to 16 | Moderate Symptoms |
| From 17 to 21 | Marked symptoms |
| From 22 to 28 | Severe symptoms |
| 1.c) Yale-Brown Obsessive-compulsive Scale (Y-BOCS) | |
| Less than 7 | Normality or subclinical condition |
| From 8 to 15 | Mild case of OCD |
| From 16 to 23 | Moderate OCD |
| From 24 to 31 | Severe OCD |
| From 32 to 40 | Extremely severe case |
| 1.d) Hamilton Anxiety Rating Scale (HAM-A) | |
| Less than 17 | Mild case |
| From 18 to 24 | Moderate case |
| From 25 to 30 | Severe case |

The different groups of patients were admitted to receive one of the two combination formulations on the basis of the diagnosis.

1) In the group with a diagnosis of disabling panic disorder and in the "anxiety" group, the administered daily dose of the combination of the invention was 100 mg of opipramol (as free base) plus 80 mg venlafaxine (as free base).

2) The group with a diagnosis of treatment-resistant depression and the one with diagnosis of obsessive-compulsive disorder received a daily dose of 120 mg of opipramol (as free base) plus 140 mg venlafaxine (as free base).

Interim evaluations were carried out at 2, 4, 8, 16 weeks from the start of therapy using the hetero-administration questionnaire called Clinical Global Impression-improvement (CGI-i).

The therapeutic treatment was administered to all groups as a single daily dose (a 24-h controlled release formulation), in the morning after breakfast.

The interim evaluations at 2, 4, 8 and 16 weeks after the start of treatment carried out using the CGI-i hetero-administration questionnaire showed a response rate of 45.6% at week 2, 61.5% at week 4, 78.4% at week 8 and 92.7 at week 16.

An especially important and unexpected finding was that the anxiety symptoms started to respond positively to the treatment as early as 72 h from the start of administration of the O/V combination of the invention, in clear contrast both with what normally occurs in trials carried out with the known SSRIs and SNRIs and with what we have been able to verify by separately administering the two active components of the combination at the doses indicated above. In particular, as many as 16 patients from the whole group of enrolled patients already showed a significant improvement after the first 36 hs from the beginning of the treatment.

Clinical Results

Patients with Obsessive-Compulsive Disorder.

After 4 months of treatment, the score based on the Y-BOCS rating scale for the nine patients with scores between 24 and 29 passed to a score equal to or less than 7, indicating passage from a severe/disabling condition to a subclinical one, therefore superimposable to normality. Only in one patient who started from a score of 32 (extremely severe disorder), the improvement presented a value of 10 points, indicating in any case a clinically highly significant improvement.

Patients with Treatment-Resistant Major Depression.

Of the 12 patients entered into the study, all with scores greater than 34 on the basis of the MADRS scale, at the sixteenth week 9 had a score of less than 6 (absence of depressive symptoms), one patient settled on a score of 8 (slight residual symptoms) and two male patients on a score of 7 (analogous to the previous case). During the following month, while continuing the therapy all patients stated that they had resumed their interests and/or their working activity.

Patients with Panic Disorder.

The 12 patients in the study, all with diagnosis of particularly severe/disabling disorder, reached a complete remission of the symptoms of panic (score 4 of the PDSS scale) at the end of the 4-month period of treatment. Of these, one female patient with agoraphobia and "used" to leaving house exclusively accompanied by trusted people, preferably the husband (companion-accompanier phenomenon), continued to want to be accompanied on her outings, but only in the event of rain, even though the core typical symptom of panic was no longer present. It should be noted that in the "panic group" 4 patients also had a diagnosis of social phobia and that the two conditions tended towards an improvement and resolution in parallel.

Patients with Generalized Anxiety Disorder and Somatized Anxiety.

The 10 patients of this group responded particularly rapidly (just by way of example, by comparison with patients who for the same clinical conditions were treated in numerous studies present in the literature with an antidepressant of the SSRI or SNRI class). 7 of these patients presented a clear improvement in the symptoms of anxiety as early as 72 hours post-treatment and of these, 4 stated that they were much less anxious already after the first 36 hours of treatment. At the end of the 16-week period, scores achieved by this group of patients according to the Hamilton Anxiety Rating Scale (HAM-A) were all lower than 17 (sub-clinical condition/normality).

The opipramol/venlafaxine combination of the present invention demonstrated under the various clinical conditions analyzed, an efficacy superior to all therapies previously administered to the patient sample, including mono-administration of the two drugs separately. A first observation particularly worthy of note relates to the exceptionally rapid response to anxiety symptomatology as compared with any other treatment with antidepressants, that is already present 36 hours after the start of treatment, in marked contrast to what normally occurs, for example, with SSRIs and SNRIs. In this sense the O/V combination of the invention represents a therapeutic approach that is unique among those concerning the use of antidepressants, whose latency of action both on the anxiety component and on the depressive component is generally not less than two weeks; in fact, the disadvantage for a patient of having to wait 14-21 days since the start of treatment with antidepressants before experiencing the first improvements is a factor that has been unexpectedly overcome with the O/V combination of the present invention, and this resulted in a considerable as well as unexpected improvement in compliance.

Furthermore, no patient stopped the therapy before the end-point evaluations at the end of the study. There were no drop-outs, nor were poorly tolerated side effects reported; only a subset of patients assigned to high dosage (120 mg of opipramol plus 140 mg venlafaxine), showed mild and transient disturbances: 5 in the depression resistant group and 7 in the group with obsessive-compulsive disorder. The disorders more frequently reported from these patients consisted in mild dry mouth and constipation, which resolved spontaneously without any adjustment of the therapy.

At the end of the study period, patients reported having recovered satisfactorily even cognitive functions, memory in particular, and in general a good efficiency in carrying out psycho-motor activities.

Clinically, these effects were expressed as a recovery of cognitive functions and of social and working behaviour.

INDUSTRIAL APPLICABILITY

The combined action of opipramol and venlafaxine on the σ-1 receptor was much stronger than could be expected from studying the action of the individual compounds. Actually, the pharmaceutical composition described and claimed in the present document has enabled the depressive and anxiety syndromes described previously to be treated advantageously and successfully, in particular: major depression, generalized anxiety disorder, social phobia, panic disorder, mixed depression and anxiety disorder, somatoform disorder, treatment-resistant depression, obsessive-compulsive disorder, especially in those cases which demonstrated to be resistant to the treatments (which with the individual compounds was not found to be feasible in an acceptable manner).

The invention claimed is:

1. A combination of Opipramol and Venlafaxine adapted for use as a medicament, wherein:
   Opipramol is present in an effective amount comprised from 60 to 200 mg if present as free base, or comprised from 72 to 240.03 mg if present as dihydrochloride; and
   Venlafaxine is present in an effective amount comprised from 75 to 225 mg if present as free base, or comprised from 84.86 to 254.58 mg if present as hydrochloride.

2. A pharmaceutical composition comprising:
   an active principle that is the combination of Opipramol and Venlafaxine according to claim 1, wherein:
   Opipramol is present in the effective amount comprised from 60 to 200 mg if present as free base, or comprised from 72 to 240.03 mg if present as dihydrochloride; and
   Venlafaxine is present in the effective amount comprised from 75 to 225 mg if present as free base, or comprised from 84.86 to 254.58 mg if present as hydrochloride.

3. The pharmaceutical composition according to claim 2, wherein:
   Opipramol is present in an amount of 100 mg or 120 mg, if present as free base, or in an amount of 120.01 mg or 152.98 mg, if present as dihydrochloride; and
   Venlafaxine is present in an amount of 80 mg or 140 mg, if present as free base or in an amount of 90.52 mg or 158.40 mg, if present as hydrochloride.

4. The pharmaceutical composition according to claim 2, further comprising one or more excipients, co-formulants, additives, preservatives, adjuvants, fillers, or extenders.

5. The pharmaceutical composition according to claim 2, wherein the pharmaceutical composition is adapted for oral administration in the form of tablets, lozenges, pastilles, pills, or soft or hard capsules.

6. The pharmaceutical composition according to claim 5, wherein the pharmaceutical composition is in a gastroresistant coated or protected form, or in a controlled release form.

7. The pharmaceutical composition according to claim 2, wherein the active principle is a combination of two active principles consisting of:
   Opipramol at 120 mg, if present as free base, or at 152.98 mg, if present as a dihydrochloride salt; and
   Venlafaxine at 140 mg if present as free base, or at 158.40 mg, if present as hydrochloride salt.

8. The pharmaceutical composition according to claim 2, wherein the active principle is a combination of two active principles consisting of:
   Opipramol at 100 mg if present as free base, or at 120.01 mg, if present as a dihydrochloride salt; and
   Venlafaxine at 80 mg if calculated as free base, and at 90.52 mg, if present as a hydrochloride salt.

9. The pharmaceutical composition according to claim 2, wherein the pharmaceutical composition is adapted for use in treating depressive and anxiety syndromes, major depression, generalized anxiety disorder, social phobia, panic disorder, mixed depression and anxiety disorder, somatoform disorder, treatment-resistant depression, or obsessive-compulsive disorder.

10. The pharmaceutical composition according to claim 7, wherein the pharmaceutical composition is adapted for use in treating major depression, generalized anxiety disorder, social phobia, panic disorder, mixed depression and anxiety disorder, somatoform disorder, treatment-resistant depression, or obsessive-compulsive disorder.

* * * * *